US007881805B2

(12) United States Patent
Bradley et al.

(10) Patent No.: US 7,881,805 B2
(45) Date of Patent: Feb. 1, 2011

(54) METHOD FOR OPTIMIZING SEARCH FOR SPINAL CORD STIMULATION PARAMETER SETTINGS

(75) Inventors: Kerry Bradley, Glendale, CA (US); James R. Thacker, Eureka, MO (US); Carla M. Woods, Beverly Hills, CA (US); John D. King, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 430 days.

(21) Appl. No.: 11/026,859

(22) Filed: Dec. 30, 2004

(65) Prior Publication Data

US 2005/0209655 A1 Sep. 22, 2005

Related U.S. Application Data

(63) Continuation-in-part of application No. 10/355,955, filed on Jan. 31, 2003, now Pat. No. 7,146,223.

(60) Provisional application No. 60/354,098, filed on Feb. 4, 2002.

(51) Int. Cl.
*A61N 1/04* (2006.01)
(52) U.S. Cl. .................. 607/117; 607/118; 607/30; 607/60; 128/920
(58) Field of Classification Search .................. 607/27, 607/59, 117, 118, 53–57, 136, 137, 141
See application file for complete search history.

(56) References Cited

U.S. PATENT DOCUMENTS

| 3,646,940 | A | 3/1972 | Timm et al. |
| 3,724,467 | A | 4/1973 | Avery et al. |
| 3,822,708 | A | 7/1974 | Zilber |
| 4,505,275 | A | 3/1985 | Chen |
| 4,793,353 | A | 12/1988 | Borkan |
| 5,167,229 | A | 12/1992 | Peckham et al. |
| 5,370,672 | A | 12/1994 | Fowler et al. |
| 5,417,719 | A | 5/1995 | Hull et al. |

(Continued)

FOREIGN PATENT DOCUMENTS

EP  0 811 395 A2  10/1997

(Continued)

OTHER PUBLICATIONS

PCT International Search Report for PCT/US2005/014533, Applicant: Advanced Bionics Corporation, Form PCT/ISA/210 and 220, dated Jan. 9, 2006 (5 pages).

(Continued)

*Primary Examiner*—Carl H. Layno
*Assistant Examiner*—Tammie K Heller
(74) *Attorney, Agent, or Firm*—Vista IP Law Group LLP

(57) ABSTRACT

A method for transitioning electrical energy in steps between electrodes implanted within a patient to stimulate tissue (e.g., spinal cord tissue) is provided. The method comprises determining a maximum comfortable step size, determining a minimum step size, selecting one or more step sizes between the maximum comfortable step size and the minimize step size, and transitioning the electrical energy between the electrodes using the selected one or more step sizes.

21 Claims, 5 Drawing Sheets

U.S. PATENT DOCUMENTS

| | | | |
|---|---|---|---|
| 5,443,486 A | 8/1995 | Hrdlicka et al. | |
| 5,626,629 A | 5/1997 | Faltys et al. | |
| 5,653,739 A | 8/1997 | Maurer et al. | |
| 5,713,922 A | 2/1998 | King | |
| 5,814,092 A | 9/1998 | King | |
| 5,893,883 A | 4/1999 | Torgerson et al. | |
| 5,895,416 A | 4/1999 | Barreras, Sr. et al. | |
| 5,913,882 A | 6/1999 | King | |
| 5,938,690 A | 8/1999 | Law et al. | |
| 6,052,624 A | 4/2000 | Mann | |
| 6,058,331 A * | 5/2000 | King | 607/62 |
| 6,083,252 A | 7/2000 | King et al. | |
| 6,308,102 B1 * | 10/2001 | Sieracki et al. | 607/59 |
| 6,381,496 B1 | 4/2002 | Meadows et al. | |
| 6,393,325 B1 | 5/2002 | Mann et al. | |
| 6,516,227 B1 | 2/2003 | Meadows et al. | |
| 6,587,724 B2 | 7/2003 | Mann | |
| 6,622,048 B1 | 9/2003 | Mann et al. | |
| 6,654,642 B2 * | 11/2003 | North et al. | 607/59 |
| 6,792,310 B1 | 9/2004 | Turcott et al. | |
| 2001/0034542 A1 * | 10/2001 | Mann | 607/30 |
| 2003/0032992 A1 | 2/2003 | Thacker et al. | |
| 2003/0114899 A1 | 6/2003 | Woods et al. | |
| 2003/0153959 A1 | 8/2003 | Thacker et al. | |
| 2004/0082980 A1 | 4/2004 | Mouine et al. | |
| 2004/0215288 A1 | 10/2004 | Lee et al. | |

FOREIGN PATENT DOCUMENTS

| | | |
|---|---|---|
| WO | WO 01/43818 A1 | 6/2001 |
| WO | WO 2004/041351 A1 | 5/2004 |

OTHER PUBLICATIONS

PCT Written Opinion of the International Search Authority for PCT/US2005/014533, Applicant: Advanced Bionics Corporation, Form PCT/ISA/237, dated Jan. 9, 2006 (4 pages).

PCT International Preliminary Report on Patentability (Chapter I of the Patent Cooperation Treaty) for PCT/US2005/014533, Applicant: Advanced Bionics Corporation, Form PCT/IB/326 and 373, dated Oct. 25, 2007 (6 pages).

PCT International Search Report for PCT/US2005/000144, Applicant: Advanced Bionics Corporation, Form PCT/ISA/210 and 220, dated Apr. 26, 2005 (3 pages).

PCT Written Opinion of the International Search Authority for PCT/US2005/000144, Applicant: Advanced Bionics Corporation, Form PCT/ISA/237, dated Apr. 26, 2005 (5 pages).

PCT International Preliminary Report on Patentability (Chapter I of the Patent Cooperation Treaty) for PCT/US2005/000144, Applicant: Advanced Bionics Corporation, Form PCT/IB/326 and 373, dated Jul. 12, 2007 (6 pages).

Office Action dated Apr. 9, 2010 in European Patent Application No. 05 711 255.9-2310, Applicant: Boston Scientific Neuromodulation Corporation, (4 pages).

* cited by examiner

TRANSITION FROM $E_1=100\%$ TO $E_2=100\%$

METHOD FOR OPTIMIZING SEARCH FOR SPINAL CORD STIMULATION PARAMETER SETTINGS

This application is a continuation-in-part of, and claims the benefit of priority to, U.S. application Ser. No. 10/355,955, filed Jan. 31, 2003, now U.S. Pat. No. 7,146,223 which claims the benefit of and priority to U.S. Provisional Application Ser. No. 60/354,098, filed Feb. 4, 2002. These prior applications are incorporated herein by reference.

BACKGROUND OF THE INVENTION

The present invention relates to Spinal Cord Stimulation (SCS) systems and more particularly to methods for efficiently searching for an effective SCS system stimulation parameter sets. An SCS system treats chronic pain by providing electrical stimulation pulses through the electrodes of an electrode array placed epidurally next to a patient's spinal cord. The stimulation parameter set determines the characteristics of the stimulation pulses provided through the electrode array, and the electrodes used to provide the stimulation pulses, which determines the electric field that is created by the stimulation. The optimal stimulation parameter set for a specific patient may be determined from the response of the patient to various sets of stimulation parameters. There is, however, an extremely large number of possible combinations of stimulation parameters, and evaluating all possible sets is very time consuming, and impractical.

Spinal cord stimulation is a well accepted clinical method for reducing pain in certain populations of patients. An SCS system typically includes an Implantable Pulse Generator (IPG), electrodes, electrode lead, and electrode lead extension. The electrodes are implanted along the dura of the spinal cord, and the IPG generates electrical pulses that are delivered, through the electrodes, to the dorsal column and dorsal root fibers within the spinal cord. Individual electrode contacts (the "electrodes") are arranged in a desired pattern and spacing in order to create an electrode array. Individual wires within one or more electrode leads connect with each electrode in the array. The electrode leads exit the spinal column and generally attach to one or more electrode lead extensions. The electrode lead extensions, in turn, are typically tunneled around the torso of the patient to a subcutaneous pocket where the IPG is implanted.

Spinal cord stimulators and other stimulation systems are known in the art. For example, an implantable electronic stimulator is disclosed in U.S. Pat. No. 3,646,940 issued Mar. 7, 1972 for "Implantable Electronic Stimulator Electrode and Method" that provides timed sequenced electrical impulses to a plurality of electrodes. As another example, U.S. Pat. No. 3,724,467 issued Apr. 3, 1973 for "Electrode Implant For The Neuro-Stimulation of the Spinal Cord," teaches an electrode implant for the neuro-stimulation of the spinal cord. A relatively thin and flexible strip of physiologically inert plastic is provided as a carrier on which a plurality of electrodes are formed. The electrodes are connected by leads to an RF receiver, which is also implanted.

In U.S. Pat. No. 3,822,708, issued Jul. 9, 1974 for "Electrical Spinal Cord Stimulating Device and Method for Management of Pain," another type of electrical spinal cord stimulation device is taught. The device disclosed in the '708 patent has five aligned electrodes which are positioned longitudinally on the spinal cord. Electrical pulses applied to the electrodes block perceived intractable pain, while allowing passage of other sensations. A patient operated switch allows the patient to adjust the stimulation parameters.

Most of the electrode arrays used with known SCS systems employ between 4 and 16 electrodes. Electrodes are selectively programmed to act as anodes, cathodes, or left off, creating a stimulating group. The number of stimulation groups available, combined with the ability of integrated circuits to generate a variety of complex stimulation pulses, presents a huge selection of stimulation parameter sets to the clinician. When an SCS system is implanted, a "fitting" procedure is performed to select an effective stimulation parameter set for a particular patient.

A known practice is to manually test one parameter set, and then select a new stimulation parameter set to test, and compare the results. Each parameter set is painstakingly configured, and ramped up in amplitude gradually to avoid patient discomfort. The clinician bases their selection of a new stimulation parameter set on their personal experience and intuition. There is no systematic method to guide the clinician. If the selected stimulation parameters are not an improvement, the clinician repeats these steps, using a new stimulation parameter set, based only on dead-reckoning. The combination of the time required to test each parameter set, and the number of parameter sets tested, results in a very time consuming process.

An example of another stimulation system that is known in the art is a cochlear implant, such as the implant and system described in U.S. Pat. No. 5,626,629, issued May 6, 1997, entitled "Programming of a Speech Processor for an Implantable Cochlear Stimulator" and incorporated herein by reference. The '629 patent describes a method for fitting a cochlear implant to a patient. The method involves determining estimated and threshold stimulation levels of one of the channels of the implant using an objective measurement, such as a measured electrically evoked physiological response. This information is used as a starting point to make further adjustments to stimulation parameters in response to subjective feedback from the patient.

Another known practice is current steering, a process that is more fully described in U.S. Pat. No. 6,393,325, incorporated herein by reference. This process greatly reduces the amount of time required to test a parameter set because the stimulation moves gradually along the array and does not need to be ramped down and then up again in between the testing of different parameter sets as in a conventional system. For example, one embodiment disclosed in the U.S. Pat. No. 6,393,325 (noted above) uses a table having stimulation parameters and a directional input device which the patient uses to navigate through the table.

What is needed is a method for selection of trial stimulation parameter sets that guides the clinician towards an effective stimulation parameter set(s). What is also needed is an algorithm to maintain constant paresthesia while stimulation is transitioned from one electrode to another.

SUMMARY OF THE INVENTION

The present invention addresses the above and other needs by providing a method for selecting trial Spinal Cord Stimulation (SCS) stimulation parameter sets, which method guides a clinician towards an effective set of stimulation parameters. The methods described herein may be implemented using software resident on a computer, a programmer, or on the stimulator itself.

In accordance with one aspect of the invention, there is provided a table, or equivalent, of a small number of trial stimulation parameter sets (a coarse table) that defines a starting point for selecting a stimulation parameter set. There is also provided a larger table (a fine table), or equivalent, of predetermined stimulation parameter sets to guide the search for a local optimum. Any method for finding an effective stimulation parameter set that uses a combination of a small coarse table, or equivalent, and a large fine table, or equivalent, is intended to come within the scope of the invention.

In accordance with another aspect of the invention, the clinician first evaluates the effectiveness of a small number of trial stimulation parameter sets from a Simplified Measurement Table comprising for example, four stimulation parameter sets. Based on the patient's assessment, the trial stimulation parameter sets are ranked. Then the clinician selects a starting row in a Simplified Steering Table corresponding to the highest ranked trial stimulation parameter set. The clinician moves either up or down from the starting row, testing consecutive parameter sets. The clinician continues as long as the patient indicates that the stimulation results are improving. When a local optimum is found, the clinician returns to the starting row, and tests in the opposite direction for another local optimum. If an acceptable set of stimulation parameters if found, the selection process is complete. If an acceptable set is not found, a new starting row in the Simplified Steering Table is selected based on the next best trial stimulation parameter set, and the process of searching for local optima is repeated.

In accordance with yet another aspect of the invention, there is provided a method for searching for an effective set of stimulation parameters for an SCS system. The method improves the efficiency of the search by organizing the search based on predetermined stimulation parameter sets. A clinician first ranks the effectiveness of a very small set of trial stimulation parameter sets, and then searches for an optimum stimulation set around the highest ranked trial stimulation parameter set.

In accordance with yet another aspect of the invention, there is provided a method for determining step size during current steering. This method involves measuring a perception threshold and a maximum threshold for a plurality of stimulation parameter sets, determining a maximum comfortable step size, determining a minimum step size, and selecting a step size between the maximum comfortable step size and the minimum step size. The minimum step size may be the desired electric field shift resolution or the minimum programmable stimulator step size and the maximum comfortable step size may be estimated in advance of the current steering procedure or may be measured prior to or as part of the procedure. This method may be used to generate or select a current steering table having desired step size(s).

In accordance with another aspect of the invention, there is provided a method for maintaining paresthesia during the transition of stimulation between electrodes. This method involves selecting a multiplier to be applied to each electrode during electrode transition, creating a Superposition Equalization ("SEQ") algorithm which uses the multiplier to determine the output of each electrode during the transition, and providing stimulation to each electrode at a magnitude determined by the SEQ algorithm. The multiplier may be determined from the lead type or characteristics such as inter-electrode distance, from measurement of bipolar impedance or the inter-electrode distance, from the comparison of a measured dual cathode threshold to single cathode thresholds, from a real-time determination using patient feedback, or from any other method that provides a meaningful multiplier. A modifying function then applies this multiplier to the unmodified output of the electrodes during the transition to adapt the energy output of the electrodes to compensate for the change in current density during the transition.

It is thus a feature of the present invention to provide a method for determining a locally optimum SCS system stimulation parameter set without requiring exhaustive testing of a multiplicity of stimulation parameter sets. Millions of possible stimulation parameter sets exist, and it is therefore impossible to test all possible sets. Therefore, the clinician must be satisfied by finding an effective stimulation parameter set. By providing a systematic method for searching for an effective stimulation parameter set, a locally optimum stimulation parameter set is found, which locally optimum stimulation parameter set is associated with a best trial stimulation parameter set.

It is also a feature of the present invention to provide a method for maintaining paresthesia while transitioning cathodes and anodes from one electrode to the next. By using a modifying function to apply a multiplier to the energy output of the electrodes, an SEQ algorithm provides for a relatively constant level of paresthesia during transition.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

Appendix A, comprising 2 pages including a cover, is an example of a Simplified Measurement Table.

Appendix B, comprising 13 pages including a cover, is an example of a Simplified Steering Table.

Appendices A and B are incorporated herein by reference.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The method of the present invention provides a systematic approach for selecting a Spinal Cord Stimulation (SCS) stimulation parameter set. The method leads a clinician through a selection process that efficiently locates locally optimum stimulation parameter sets.

Figures 1, 2:
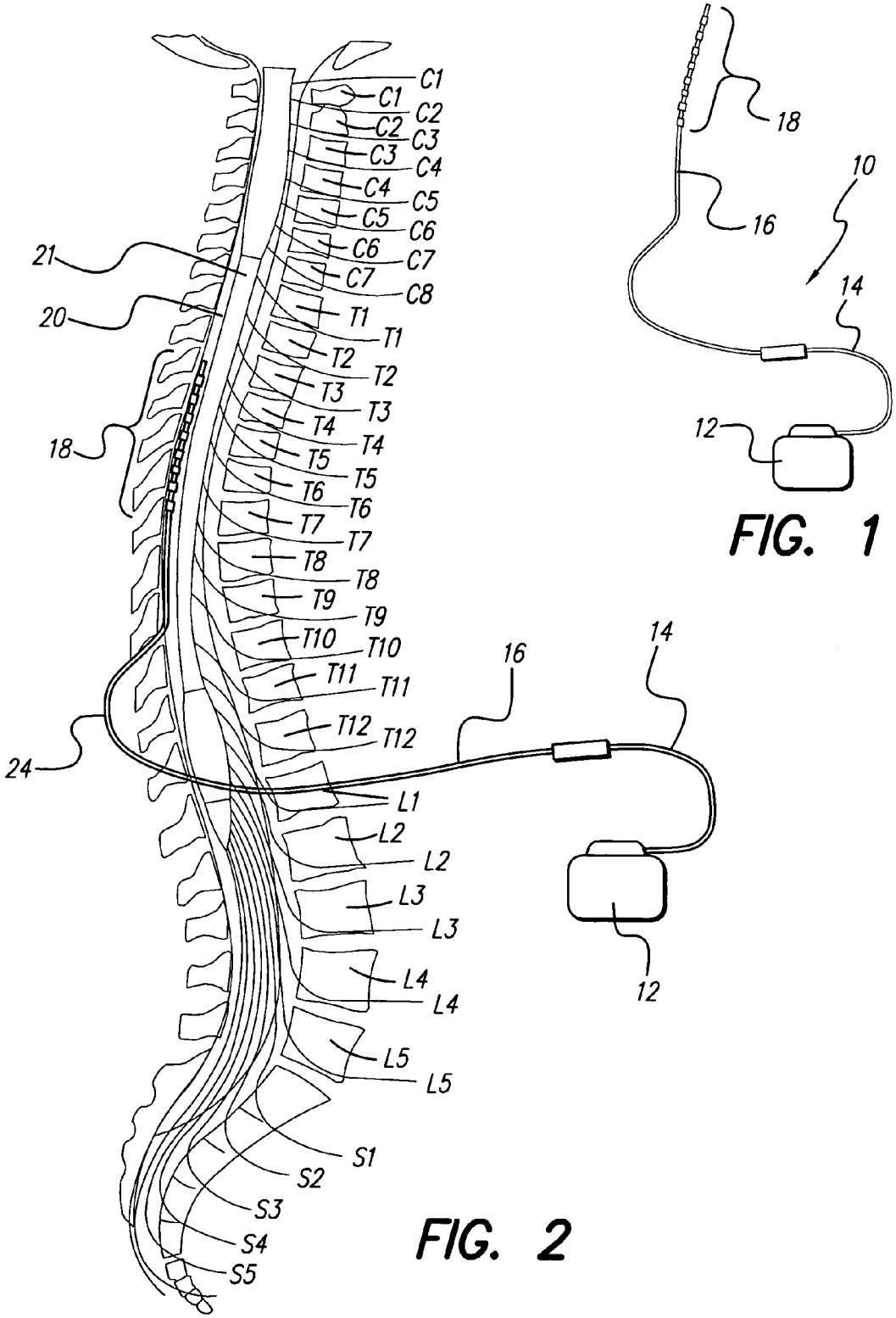
FIG. 1 shows a Spinal Cord Stimulation (SCS) system.
FIG. 2 depicts the SCS system of FIG. 1 implanted in a spinal column.

A typical Spinal Cord Stimulation (SCS) system 10 is shown in FIG. 1. The SCS system 10 typically comprises an Implantable Pulse Generator (IPG) 12, a lead extension 14, an electrode lead 16, and an electrode array 18. The IPG 12 generates stimulation current for implanted electrodes that make up the electrode array 18. A proximal end of the lead extension 14 is removably connected to the IPG 12 and a distal end of the lead extension 14 is removably connected to a proximal end of the electrode lead 16, and electrode array 18 is formed on a distal end of the electrode lead 16. The in-series combination of the lead extension 14 and electrode lead 16, carry the stimulation current from the IPG 12 to the electrode array 18.

The SCS system 10 described in FIG. 1 above, is depicted implanted in the epidural space 20 in FIG. 2. The electrode array 18 is implanted at the site of nerves that are the target of stimulation, e.g., along the spinal cord 21. Due to the lack of space near the location where the electrode lead 16 exits the spinal column, the IPG 12 is generally implanted in the abdomen or above the buttocks. The lead extension 14 facilitates locating the IPG 12 away from the electrode lead exit point.

A more detailed description of a representative SCS system that may be used with the present invention is described in U.S. Pat. No. 6,516,227, issued 4 Feb. 2003, incorporated herein by reference. It is to be emphasized, however, that the invention herein described may be used with many different types of stimulation systems, and is not limited to use only with the representative SCS system described in the U.S. Pat. No. 6,516,227.

Figure 3:
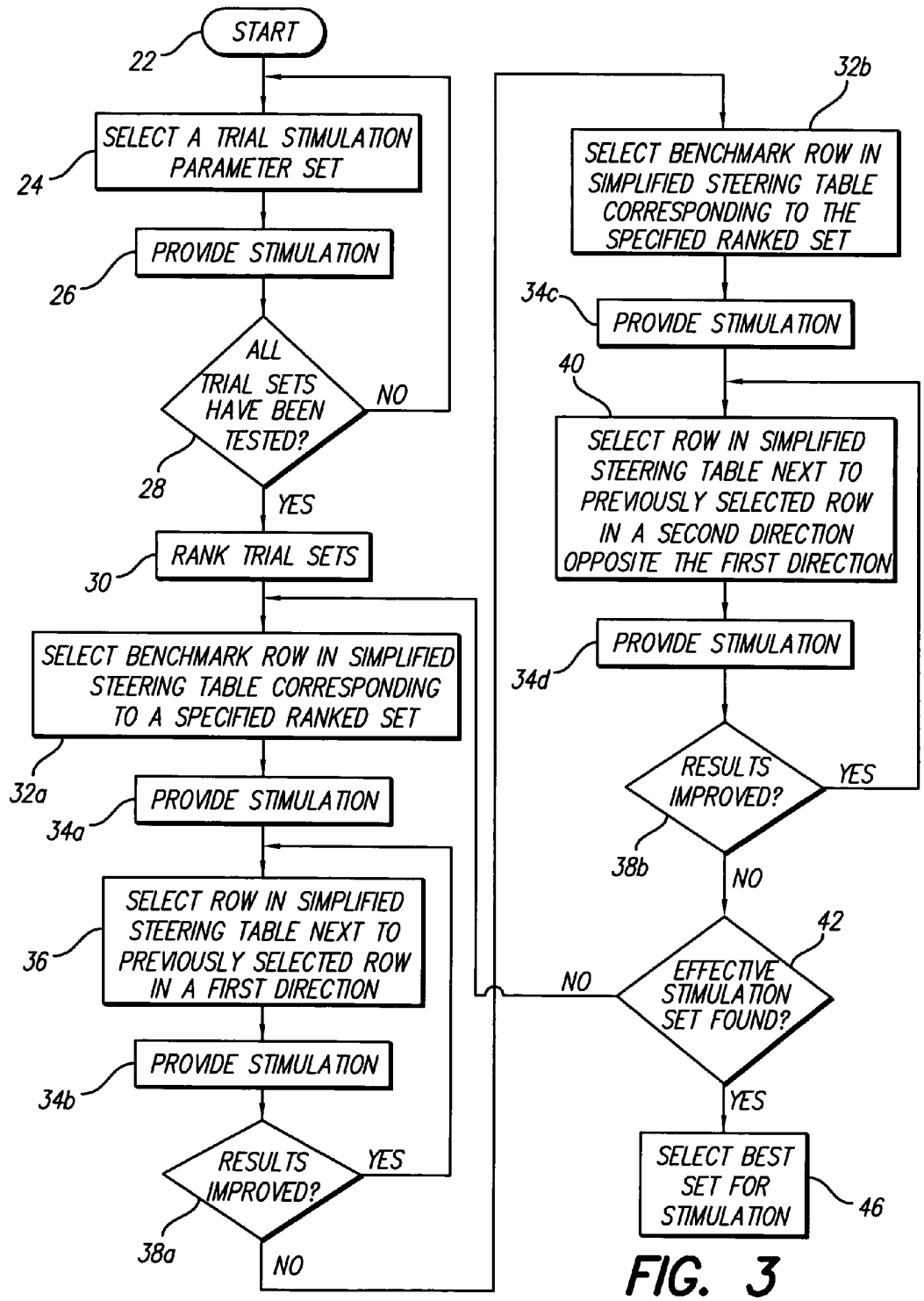
FIG. 3 depicts a stimulation parameter set flow chart according to one embodiment of the present invention.

A flow chart representing one embodiment of a method for stimulation parameter set selection in accordance with the present invention is depicted in FIG. 3. As with most flow charts, each step or act of the method is represented in a "box" or "block" of the flow chart. Each box or block, in turn, has a reference number associated with it to help explain the process in the description that follows.

At the start 22 of the method, a measurement table, or equivalent, and a steering table, or equivalent, are provided. The measurement table typically comprises rows, with each row defining one set of stimulation parameters. In a preferred embodiment, each row specifies the polarity on each electrode of the electrode array 18 (FIGS. 1 and 2) that the stimulation system determines should be applied to the patient for a particular purpose. The electrode array 18 preferably comprises eight or sixteen electrodes, but the measurement table may only utilize a subset of the electrode array 18, for example four electrodes. Those skilled in the art will recognize that a measurement table may include stimulation parameter sets with various variations, such as pulse duration or pulse frequency, and a measurement table with such other variations is intended to come within the scope of the present invention. An exemplary simplified measurement table that may be used with the invention is found in Appendix A.

The steering table, or equivalent, typically includes a larger number of rows than does the measurement table. An exemplary steering table, containing 541 rows, that may be used with the invention is found in Appendix B. The rows in the steering table typically reflect the same variation as the rows in the measurement table, however, those skilled in the art will recognize that the steering table may also include other degrees of variation not included in the measurement table, and these variations are also intended to come within the scope of the invention. At least one row in the steering table will however correspond to one of the rows in the measurement table, as will be made apparent by the following description.

The rows in the steering table are arranged in order based on the physical characteristics of the stimulation provided by each stimulation parameter set, so that "transitioning" i.e., moving from one row to the next in the steering table, represents a gradual, and somewhat uniform, change in the parameters of the delivered stimulation. In other words, stepping from one row to an adjacent row in the steering table causes the stimulation applied to the tissue through the individual electrodes of the electrode array 18 to gradually move in a desired direction. This type of current steering is described more fully in U.S. Pat. No. 6,393,325, noted above.

As described in more detail below, the steering table initially provided may be modified or "filled in" following testing of the trial stimulation parameter sets, determination of the maximum comfortable step size, or determination of the desired electric field shift resolution in order to optimize the step sizes that are employed for transitioning from one stimulation parameter set in the steering table to the next.

Once the desired measurement table and steering table have been provided, the first step in the method is selection of a trial stimulation parameter set for testing (block 24). Generally, the first row of the measurement table will be tested first, followed in order by the remaining rows. However, the order of row selection is not essential, and the rows may be selected in any order. Next, the selected stimulation parameter set is used to provide stimulation to the patient (block 26). Generally, to avoid uncomfortable "jolting" and over-stimulation, the amplitude of the stimulation provided is initially set to a relatively low level, i.e., below the level that will result in the patient perceiving paresthesia. The amplitude is then gradually increased. The stimulation level at which the patient begins to perceive paresthesia is called the perception or perceptual threshold. See e.g., U.S. Pat. No. 6,393,325, noted above. The stimulation is then increased until it begins to become uncomfortable for the patient. This level is called the maximum or discomfort threshold. See e.g., U.S. Pat. No. 6,393,325, noted above. These pre-steering measured thresholds may be noted and used later in the steering process. Alternatively, these thresholds may be determined based on pre-established values, or based on previously-measured thresholds for the patient.

The patient provides feedback as to the effectiveness of the stimulation that is applied using the trial stimulation parameter set. Alternative means (e.g., objective measurements of various physiological parameters of the patient, such as perspiration, muscle tension, respiration rate, heart rate, and the like) may also be used to judge the effectiveness of the applied stimulation. A determination is then made if all of the trial sets have been tested (block 28). The steps of selecting a trial set of stimulation parameters (block 24) and providing stimulation in accordance with the selected trial set of stimulation parameters (block 26) are repeated until all of the trial stimulation parameter sets have been tested.

After all of the trial stimulation parameter sets have been tested, the trial stimulation parameter sets are ranked (block 30) based upon the patient's evaluation (and/or based upon alternative evaluation of selected physiological parameters of the patient) of the effectiveness of each trial stimulation parameter set.

The testing and ranking of the trial stimulation parameter sets provides a coarse approximation of the stimulation which may be most effective. Because the trial stimulation parameter set is only a coarse approximation, the implication is that fine adjustments of such parameter sets may also be effective, and perhaps even more effective. Hence, once the trial stimulation parameter sets have been ranked, the highest ranked trial stimulation parameter set becomes a first specified ranked set that functions as a first "benchmark," or starting point, for a much finer search for the most effective stimulation parameter set. The finer search for a stimulation parameter set begins by selecting a row in the steering table that corresponds to the highest ranked set in the measurement table (block 32*a*). This selected highest ranked trial stimulation parameter set is then used to provide stimulation (block 34*a*) to the patient. Again, the patient evaluates the effectiveness of the stimulation, and/or alternative means (e.g., measuring physiological parameters of the patient) are used to evaluate the effectiveness of the stimulation. Then, a row next to the row just tested, e.g., moving in a first direction in the steering table, such as down, is selected as a possible new stimulation parameter set (block 36), and this new row is then used to provide stimulation (block 34*b*). The results of the new stimulation are then compared to the results of the previous stimulation (block 38*a*). If the results improve (YES branch of block 38*a*) the steps set forth in blocks 36 and 34*b* are repeated, i.e., the row in the steering table adjacent to the most recently used row, moving in the same direction in the table as before, is used to define a new stimulation parameter set (block 36) and that stimulation parameter set is used to provide stimulation (block 34*b*). As long as the stimulation results continue to improve, this process of stepping to the next row in the steering table and retesting is continued, thereby fine tuning the stimulation parameter set until no further improvements are detected.

As soon as the results fail to improve (NO branch of block 38), the method goes back to the "benchmark" parameter set, i.e., that row in the steering table corresponding to the highest ranked set (block 32*b*) and stimulation is again provided (block 34*c*). This is actually a repeat of the stimulation performed at blocks 32*a* and 34*a*, but inasmuch as one or more stimulation parameter sets have been provided since the benchmark stimulation was provided at steps 32*a* and 34*a*, this repeat stimulation provides the patient with a reminder or refresher of what the benchmark stimulation was like. (Alternatively, of course, this repeat of the benchmark stimulation could be skipped.) Then, a process almost identical to that described above is performed to again fine tune the benchmark stimulation parameter set, only in the other direction. That is, the row adjacent to the row that defines the benchmark stimulation parameter set is selected as the row that defines the stimulation parameter set (block 40), moving in the opposite direction, e.g., up, from the direction used in the step performed at block 36. Once a row is selected, stimulation is provided using the parameters of the selected row (block 34*d*). Thus, the fine tuning that occurs at steps 40 and 34*d* in FIG. 3 occurs while moving in the opposite direction in the steering table than was used previously.

The results of the new stimulation applied at step 34*d* are compared to the results of the previous stimulation (block 38*b*). If the results improve (YES branch of block 38*b*), the steps set forth in blocks 40 and 34*d* are repeated, i.e., the row in the steering table adjacent to the most recently used row, moving in the same direction in the table as before, are used to define a new stimulation parameter set (block 40), and that stimulation parameter set is used to provide stimulation (block 34*d*). As long as the stimulation results continue to improve, this process of stepping to the next row in the steering table, and retesting is continued, thereby fine tuning the stimulation parameter set until no further improvements are detected.

Hence, it is seen that thus far in the method, two sets of effective stimulation parameters have been identified: one by moving in a first direction from the benchmark row (of the specified ranked set) in the steering table (determined using the steps at blocks 36, 34*b* and 38*a*), and another by moving from the benchmark row in a second direction in the steering table (determined using the steps at blocks 40, 34*d* and 38*b*). These two possible stimulation sets are then evaluated to see if one comprises the most effective stimulation set (block 42). If so (YES branch of block 42), then that set is selected as the best parameter stimulation set for the stimulation that is to be provided (block 46) whenever the operating program of the SCS system (or other neural system) determines stimulation is needed. If not (NO branch of block 42), then the search continues for the most effective stimulation set by selecting the row in the steering table corresponding to the next highest ranked set (block 44), e.g., the second ranked stimulation set. The next highest ranked set thus defines a new specified "benchmark" stimulation set from which additional fine tuning is performed as described above (blocks 32*a* through 38*b*).

It is thus seen that unless an effective stimulation parameter set is found at block 42, the process described in FIG. 3 is repeated for the next highest ranked trial stimulation parameter set, until the most effective stimulation parameter set is identified.

By way of a simple example, consider the Simplified Measurement Table found in Appendix A and the Simplified Steering Table found in Appendix B. After testing each of the stimulation parameter sets defined by the rows in the Simplified Measurement Table in Appendix A, the following "coarse" ranking in effectiveness of the stimulation sets is found:

| Stimulation Set | Rank |
|---|---|
| 3 | 1 |
| 1 | 2 |
| 2 | 3 |
| 4 | 4 |

Starting with the highest ranked Stimulation Set (from the Simplified Measurement Table in Appendix A), which uses Electrode Number 3 as an anode (+) and Electrode Number 5 as a cathode (−) to provide a stimulus to the patient, a corresponding row in the Simplified Steering Table (in Appendix B) is found to be Stimulation Set No. 301, which shows that the current flow from Electrode 3 is "1" and the current flow from Electrode 5 is "−1". This means that all of the current applied by the stimulator is applied from Electrode 3 as an anode to Electrode 5 as a cathode. (The amplitude of the current applied may, of course, be adjusted as required.) Thus, the coarse adjustment provided by the measurement table leads one to Stimulation Set No. 301 in the Simplified Steering Table. Stimulation Set No. 301 thus serves as the first "benchmark" stimulation set.

Once the first benchmark stimulation set is identified, the method then fine tunes this selection by applying the stimulation set(s) adjacent the benchmark set. For example, going "down" in the Simplified Steering Table, Stimulation Set No. 302 is applied, then No. 303, and then No. 304, and so on, until the patient (or other means) determines that no further improvement results. In this example, Stimulation Set No. 302 is found to be the most effective set.

In a similar manner, going "up" in the Simplified Steering Table from the benchmark set No. 301), Stimulation Set No. 300 is applied, then No. 299, then No. 298, and so on, until the patient (or other means) determines that no further improvement results. In this example, Stimulation Set 298 is found to be the most effective set to use.

Once the two Stimulation Sets No. 298 and 302 have been identified, then a determination is made as to which one is the most effective to use for stimulation. If one of these two is the most effective, e.g., Stimulation Set No. 298, then that Stimulation Set is selected as the best one to use for stimulation in this instance, and the search ends. If, however, neither is found to be the most effective, then the process continues by locating the second-highest ranked benchmark stimulation set (corresponding to Stimulation Set No. 1 in the Simplified Measurement Table) in the Simplified Steering Table. As seen from the Simplified Measurement Table, Stimulation Set No. 1 defines Electrode No. 1 as a cathode and Electrode No. 3 as an anode. This corresponds to Stimulation Set No. 21 in the Simplified Steering Table. Hence, fine tuning of this benchmark stimulation set is conducted by first going "down," and then "up" from Stimulation Set No. 21 until the stimulation set is found that does not result in any further improvement.

The two stimulation sets identified from fine tuning the second benchmark stimulation set (one by moving "down" from the benchmark row and the other by moving "up" from the benchmark row) are then evaluated to determine if one if the most effective to use for stimulation. If one of these two is the most effective, then that stimulation set is selected as the best one to use for stimulation in this instance, and the search ends. If, however, neither is found to be the most effective, then the process continues by locating the third-highest ranked benchmark stimulation set (corresponding to Stimulation Set No. 2 in the Simplified Measurement Table) in the Simplified Steering Table, and the process continues as described.

Those skilled in the art will recognize that various variations exist to the method described herein. For example, a gradient method may be utilized to evaluate the slope of stimulation parameter set effectiveness around each trial stimulation parameter set. A combination of the relative effectiveness of each trial stimulation parameter set, and the slope of the effectiveness in the neighborhood of the trial stimulation parameter set may be used to select which trial stimulation parameter set to test around. The basic core of the present invention is to use a table, or equivalent, of a small number of trial stimulation parameter sets (a coarse table) to determine a starting point, and a larger table (a fine table), or equivalent, of predetermined stimulation parameter sets to guide the search for a local optimum. Any method for finding an effective stimulation parameter set that uses a combination of a small coarse table, and a large fine table, is intended to come within the scope of the invention.

In order to make the search for the optimal stimulation parameters even more efficient, a method for selecting the step sizes in the fine table is used. This method takes into account various factors, such as the maximum and perception thresholds at various points in the table, in order to determine the most efficient step size.

In the fine table provided in Appendix B, step sizes of a fixed percentage (e.g., 5 or 10%) are used. In clinical practice, fixed step sizes of 10% are often used. However, a fixed step size of 10% may be too large under certain circumstances, and may exceed the patient's maximum comfortable step size, resulting in discomfort to the patient. If a lower fixed step size were chosen (e.g., 1%), that step size may be too small under certain circumstances, and may be smaller than the resolution of the spinal cord stimulator. Similarly, a smaller step size (e.g., 1%) may be so small that time is wasted transitioning from one row in the table to the next in the course of evaluating stimulation parameters that produce similar, potentially ineffective results.

The example of a patient being treated for severe back pain illustrates this problem. It would not be unusual for such a patient to require stimulation having an cathodic amplitude of 8 milliamperes (mA) and a pulse width of 1000 microseconds (As). A 10% step size (i.e., a change of 0.8 mA in each step) would result in a change in stimulation charge of 800 nanocoulombs per pulse (nC/pulse). Empirical estimates using clinical data suggest that the typical maximum comfortable step size is one that results in a 100 nC/pulse change in stimulation charge. An 800 nC/pulse change is well above this estimated maximum and would almost certainly result in an uncomfortable "jolt" to the patient. Repeated "jolting" may become so uncomfortable that the patient and/or clinician will refuse to use current steering in the fitting process. Thus, a more appropriate step size given these stimulation parameters would be 1%. A 1% step size would result in an 80 nC/pulse change in stimulation charge, which is below the estimated 100 nC/pulse maximum.

However, when lower levels of stimulation are used, a fixed 1% step size is inappropriate. In the case where a patient requires stimulation having an amplitude of 3 mA and pulse width of 1000 µs, a 1% step size would produce a 0.03 mA change in amplitude. This is less than the resolution of many spinal cord stimulation systems. Furthermore, such small step sizes would mean that a greater number of steps would be required when transitioning through this portion of the table. If this portion of the table were not producing effective results, then a great deal of time would be wasted "passing through" stimulation configurations that are not beneficial in order to get to better configurations.

Figure 9:
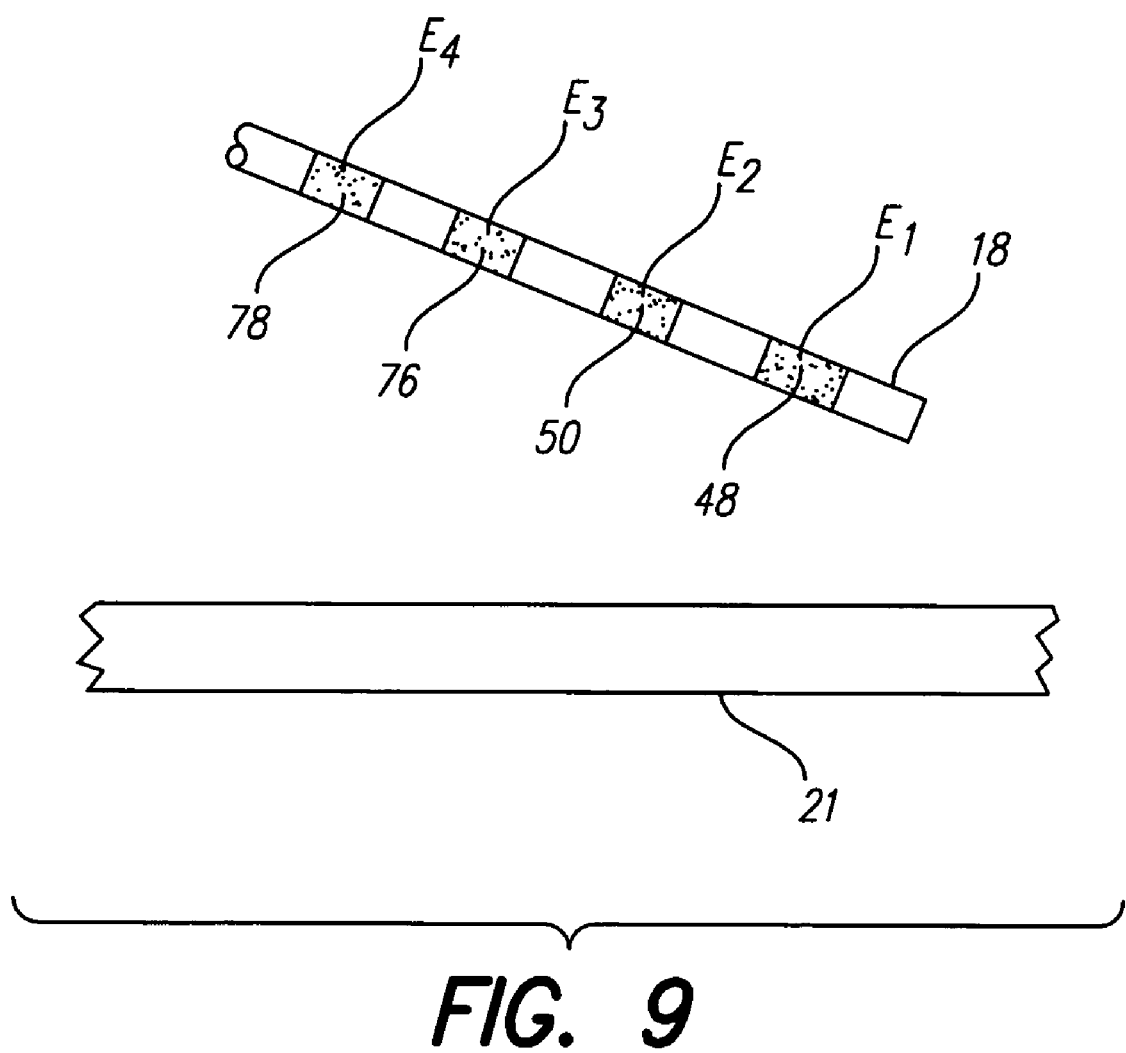
FIG. 9 depicts a lead having electrodes located at varying distances from a spinal cord.

The example shown in FIG. 9 also illustrates this point. In FIG. 9, the various electrodes $E_1$ 48, $E_2$ 50, $E_3$ 76 and $E_4$ 78 are located at different distances from the spinal cord 21. This is not uncommon as electrode arrays, once implanted, are often not perfectly parallel to and aligned with the spinal cord. As a result, in this example, the nominal amplitude required for each electrode alone to provide adequate stimulation to induce paresthesia in the spinal cord may be as follows: $E_1$=3 mA, $E_2$=4 mA, $E_3$=6 mA, $E_4$=8 mA. As explained above, no single fixed percentage step size for transitioning from $E_1$ to $E_4$ would be appropriate. A 5 or 10% step size could produce a "jolt" for current amplitudes near those associated with $E_4$, while a 1% step size would be too small for currents near those associated with $E_1$, wasting clinical time (if the spinal cord stimulator even had a resolution small enough to make 1% step sizes in this current range).

In order to determine appropriate and efficient step sizes for a particular portion of a steering table, the perception threshold and maximum threshold levels for one or more trial stimulation parameter sets are first determined, as discussed above. Trial stimulation parameter sets usually define stimulation pulses spaced somewhat equally along the electrode array, so as to provide meaningful data for different portions of the array. The optimal stimulation level is somewhere between the perception and maximum thresholds, and may vary at different positions along the array.

Once thresholds for trial stimulation parameter sets are determined, the process of "filling in" the steering table for those configurations between the trial stimulation parameter sets can begin. Some number of intermediate configurations or "steps" are required to smoothly transition from one trial stimulation parameter set along the array without causing discomfort to the patient. The patient's maximum comfortable step size can be used as a factor to determine the number of steps needed. An estimated maximum comfortable step size may be used, such as 100 nC/pulse, or the individual's maximum comfortable step size may be measured in the clinic, such as by gradually increasing the step size of a test transition until the patient reports that it is uncomfortable. Each step in the steering table would be required to be smaller than this maximum comfortable step size. For areas along the array having relatively high thresholds, i.e., areas where higher stimulation currents are required to induce paresthesia, this requirement will result in relatively smaller percentage changes in stimulation amplitude between steps. For areas along the array having relatively lower thresholds, a larger percentage change in stimulation amplitude between steps may be used without exceeding the maximum comfortable step size.

An additional factor that may be used to determine step size is the desired electric field shift resolution or spatial resolution. Each time the stimulation parameter set is changed, the electric field produced by the stimulation changes, or "shifts." The electric field shift resolution is the minimum change in stimulation parameters required to produce a noticeable physiological difference in the effects of stimulation. It is unproductive to test multiple stimulation parameter sets that will all produce the same physiological response. Thus, the step size should be at least as large as the minimum electric field shift resolution in order to test truly "different" stimulation parameter sets and to avoid wasting clinical time. See discussion in U.S. Pat. No. 6,393,325, noted above.

Similarly, smaller step sizes may be used in regions along the array that have been previously identified as providing the best results. In such regions, the desired electric field shift resolution is small. For example, relatively smaller steps sizes (i.e., values close to the minimum electric field shift resolution) may be used when steering parameter values around (or relatively closer to) the trial stimulation parameter set that produced the best results. Additionally, if the patient identifies a region in the steering table that provides good results during the steering process, the step sizes in and around that region might be decreased, even down to the limit of the smallest programmable step size in the stimulator, so that an even more optimal stimulation parameter set may be identified.

In contrast, for those regions identified as not providing effective stimulation parameters (e.g., trial stimulation parameter sets that the patient identified as less effective), the step size should be increased to a relatively larger size (i.e., to near the maximum comfortable stimulation step size) in order to reduce the time spent "passing through" such stimulation parameters. Thus, if an initial trial stimulation parameter set does not produce effective results, large step sizes should be used in that region, up to the maximum comfortable step size. Likewise, relatively larger step sizes may be used for stimulation parameters sets that are relatively farther from trial stimulation parameter sets that the patient identified as effective.

Clinical studies of current steering have shown that shifts in anodic pulse parameters often do not produce the same paresthesia variability as cathodic shifts on stimulation arrays with relatively large electrode spacing. Thus, relatively larger step sizes may be chosen for anodic current shifts. However, the same methods for determining optimal step size described above may be applied to anodic shifts as well as cathodic shifts. Additionally, the same methods may be applied to other stimulation parameters, such as voltage amplitude, pulse width, pule rate, etc.

In another embodiment, the pre-steering measured thresholds (perception threshold and maximum threshold) may be used to select a fixed percentage table stored in memory. In this embodiment, the programmer or implant device memory contains numerous fixed percentage tables. The pre-steering measured thresholds are used to select which table provides the appropriate step size to provide meaningful spatial resolution but also to avoid exceeding the maximum comfortable step size. Variations of this embodiment are also possible. For example, the pre-steering measured thresholds may be used to select various portions of tables stored in memory for different portions of the electrode array. Combinations of these embodiments are also possible. For example, the pre-steering measured thresholds may be used to "fill-in" the entries of a steering table such that the step size is based on these thresholds. The optimal stimulation level for a trial stimulation parameter set is selected at a level between the perception threshold and the maximum threshold. This optimal level is then used to create fixed percentage steps in a steering table, provided that those steps fall within a range not exceeding the maximum comfortable step size or falling below the desired electric field shift resolution. If the fixed percentage steps do fall outside of this range, then the step size is adjusted so as to fall within the range.

Furthermore, the methods described above are not limited to use with a steering table. Although these methods may be used to "fill in" or select a current steering table, they may also be implemented using equations with variable weighting factors. For example, the estimated or maximum comfortable step size may be weighted against the desired electric field resolution to provide a step size during current steering in which no table is used. Similarly, analog or digital hardware with variable component values may be used to provide a step size during a fitting procedure.

One primary goal in current steering is to maintain paresthesia at a relatively constant intensity while transitioning stimulation provided by cathodes (and anodes) from one electrode to the next. However, the amount of current needed to create a particular level of paresthesia varies depending on the distance of the electrode (or electrodes) providing stimulation from the target of stimulation and the characteristics of the surrounding tissue. An algorithm that transitions the energy from one electrode to another in a linear fashion by only maintaining a total emission energy (e.g., 100%-0%, 90%-10%, . . . , 10%-90%, 0%-100%) will result in an unequal current density pattern.

Thus, an electrode that is at an appreciably further distance from the target tissue will require a higher output in order to provide the same level of paresthesia than one that is closer to the target tissue. On the other hand, if electrodes are closely spaced on a lead, the gradual transition of stimulation from one electrode to an adjacent electrode is likely to result in a lesser change in the perceived intensity of the stimulation, because both the new and old electrode are approximately the same distance from the target tissue. However, if electrodes are spaced far apart on a lead, the gradual transition of stimulation from one electrode to an adjacent electrode may result in loss of paresthesia during the transition, because the total stimulation reaching a particular location may fall below the perception threshold.

In order to maintain a constant level of paresthesia, the patient or clinician often must constantly adjust the stimulation amplitude "up" to avoid a loss of paresthesia and then "down" to avoid an over-stimulation condition during the fitting process. This is a time-consuming and often uncomfortable process that increases the time spent steering and the stress on the patient. As the fitting process becomes longer and more difficult, the typical patient's willingness and ability to provide meaningful feedback decreases. Thus, a fitting process in which more sets of stimulation parameters can be tested in a shorter amount of time with less discomfort to the patient has a greater chance of providing a better "fit" or end result to the patient.

In order to maintain paresthesia while electrodes are gradually transitioned, a superposition equalization (SEQ) algorithm may be used. In this method, for each change in the current distribution, there is a multiplier that is used to compensate for the physical characteristics of the lead array, i.e., electrode separation and size. A modifying function is used to apply this multiplier to the electrode energy output during transition to maintain a relatively constant current density.

Figure 4:
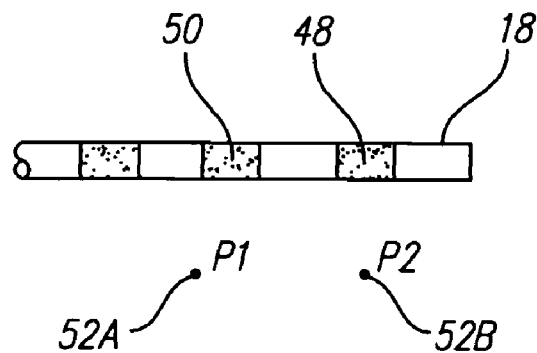
FIG. 4 depicts a portion of the electrode array 18 shown in FIG. 2 as well a target of stimulation.
Figure 5:
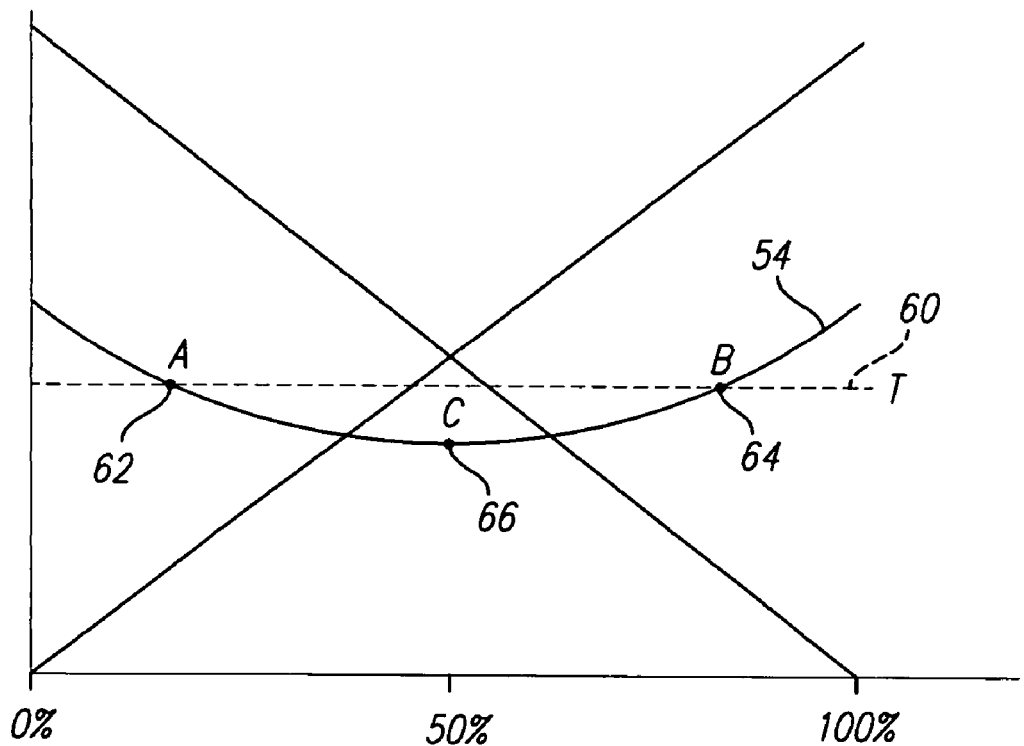
FIG. 5 depicts a graph showing stimulation levels during a transition in stimulation without the use of an SEQ algorithm.

The need for such an SEQ algorithm can be understood from an examination of conventional steering without the use of an SEQ algorithm. FIG. 4 shows a portion of a conventional lead having at least two electrodes $E_1$ 48 and $E_2$ 50. The targets of stimulation are shown as points P1 52A and P2 52B, which may be assumed to have the same threshold. FIG. 5 shows a line 54 representing the stimulation perceived by the patient as stimulation is transitioned from $E_1$ to $E_2$ in a linear fashion, e.g., $E_1$=100%, $E_2$=0%; $E_1$=95%, $E_2$=5%, . . . , $E_1$=0%, $E_2$=100%, shown by lines 56 and 58, respectively. An example of such a transition is given in the simplified steering table shown in Appendix B. Lines 21 to 41 in that table show a linear transition from electrode 3 providing 100% of the anodic stimulation to electrode 4 providing 100% of the anodic stimulation in steps of 5%.

The dashed line marked T 60 is the threshold stimulation level necessary to induce paresthesia by stimulation at either point P1 or P2. The intensity of perceived paresthesia, as represented by the line 54, is generally a curved line, because paresthesia is primarily due to activation of fibers near each electrode, and the typical range of stimulation is about 50% above the perception threshold. In this example, the curved line 54 is shown as a symmetrical, parabolic-shaped curve. In practice, line 54 would tend to be uneven and unsymmetrical, depending on the physical characteristics of the tissue and limited superposition effect of the stimulation provided by each electrode.

In this example, the curved line 54 falls below the threshold stimulation level 60 during part of the transition from $E_1$ to $E_2$. This results in the patient perceiving a loss of paresthesia at point A 62 and during the transition through the electrode combinations between point A and point B 64. Because the patient would sense no paresthesia, the patient would be unable to provide any feedback regarding whether those configurations were effective.

In order for the patient to be able to provide effective feedback, the patient or clinician would need to be given the ability to manually adjust the stimulation amplitude upward in order to create the perception of paresthesia. In fact, the patient or clinician would need to constantly increase the stimulation amplitude between point A and point C 66. This need for repeated manual adjustment of stimulation amplitude can be time-consuming and frustrating for the patient.

The use of an SEQ algorithm to maintain paresthesia at a relatively constant level during transition between electrodes addresses this problem. The SEQ algorithm adapts the total energy output to compensate for the change in current density based upon the electrode separation and electrode size. For each change in the current distribution, a modifying function uses a multiplier (M) to compensate for the lead array to maintain a relatively constant paresthesia intensity. This multiplier is applied via the modifying function to each electrode energy output during electrode transitions. In the preferred embodiment, the multiplier is applied to each electrode current output during cathodic transitions, but the multiplier may also be applied during anodic transitions or during both cathodic and anodic transitions and may be applied to other parameters such as voltage, pulse width, and pulse rate.

Relatively larger inter-electrode spacing on a lead generally requires the use of a larger multiplier, while closer inter-electrode spacing on a lead requires relatively smaller multipliers. This is due to the fact that there is less superposition effect as the inter-electrode spacing on a lead increases.

There are many different possible methods for choosing an appropriate multiplier and the examples provided below are not intended to be limiting. Any method that produces a meaningful multiplier is intended to fall within the scope of the invention.

One method for determining an appropriate multiplier is the use of a software user interface application containing a database of various electrode types. The clinician simply enters the electrode model number and/or electrode size and spacing information. The software then retrieves the appropriate multiplier corresponding to that lead model or those lead characteristics. The database may also contain the algorithm for implementing that multiplier, as discussed below.

As already mentioned, electrodes having relatively larger inter-electrode spacing require a relatively larger multiplier. For example, the Medtronic model number 3487A lead has a relatively large 9 mm inter-electrode space. Such a lead might require a multiplier of 1.6. In contrast, the Advanced Bionics model number ABSC2108 lead has a relatively smaller 4 mm inter-electrode space. This lead would require a relatively smaller multiplier, e.g., 1.2.

The multiplier may also be measured physiologically, either directly or indirectly by measuring inter-electrode spacing. For example, the clinician could measure the inter-electrode distance between two electrodes using an impedance measurement technique. This distance could then be used to select an appropriate multiplier. This method is useful for measuring appropriate multipliers for electrodes on two different leads, where the inter-electrode distance depends on where the leads were implanted and to what extent the leads have moved since surgery and whether the inter-electrode distance changes as a function of the patient's body movements. Inter-electrode spacing could also be measured using one of the many well-known standard imaging techniques, such as those involving x-rays and fluoroscopes.

The multiplier may also be measured more directly by measuring the stimulation threshold for two single cathodes and then the threshold when both of those cathodes are stimulated and then comparing the two to determine the multiplier.

Yet another way to measure the multiplier is by use of a "real time" determination using input from the patient. One electrode is stimulated and then the stimulation is transitioned to another electrode without the use of a multiplier. During the transition, the patient is told to manually adjust the level of stimulation to maintain a constant level of paresthesia throughout the transition. The adjustments made by the patient are recorded, and the multiplier can be determined from those adjustments.

Once a multiplier is selected, the SEQ algorithm can be used to maintain constant paresthesia during electrode transitions. The use of the multiplier in the SEQ algorithm is described below. In the described embodiment below, the SEQ algorithm applies the multiplier using a linear modifying function during the transition. However, one skilled in the art will appreciate that this multiplier could be applied in a non-linear fashion as well. Additionally, in the embodiment described below, the SEQ algorithm applies the multiplier to the amplitude of the current provided by the spinal cord stimulator. However, one skilled in the art will appreciate that a multiplier could also be applied to the voltage, pulse width, pulse rate, or other characteristic of the stimulation being provided, and could apply to other types of devices in addition to spinal cord stimulators.

Figure 6:
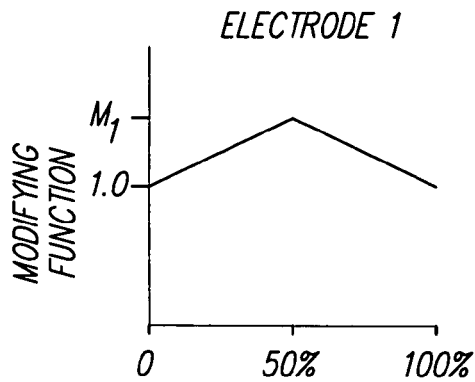
FIG. 6 depicts the output of a linear modifying function applied to electrode $E_1$.
Figure 7:
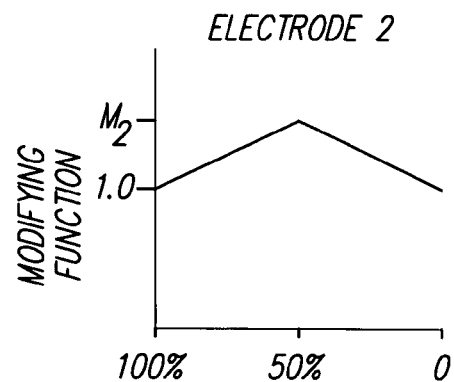
FIG. 7 depicts the output of a linear modifying function applied to electrode $E_2$.

FIGS. 6 and 7 illustrate the application of a multiplier to each of electrodes $E_1$ and $E_2$ during a transition from 100% stimulation on $E_1$ to 100% stimulation on $E_2$. Although $E_1$ 48 and $E_2$ 50 are shown as adjacent electrodes on a single lead, they could be any two electrodes on a single lead or could be located on different leads. FIG. 6 illustrates the application of a multiplier ($M_1$) to $E_1$ as the stimulation is transitioned from 100% on $E_1$ to 0% on $E_1$. For each percentage value between 100 and 0, the modifying function is defined by the graph shown in FIG. 6. For example, when $E_1$ is providing 100% of the stimulation, the modifying function provides a value of 1. As $E_1$ provides a lower relative percentage of stimulation, the modifying function value increases, until it equals $M_1$ when $E_1$ is providing 50% of the stimulation. As $E_1$ transitions to provide less than 50% of the stimulation, the modifying function value decreases, until it returns to 1 at $E_1=0\%$.

FIG. 7 illustrates the application of a multiplier ($M_2$) to $E_2$ as the stimulation is transitioned from 0% to 100% on $E_2$. For each percentage value between 0 and 100, the modifying function is defined by the graph shown in FIG. 7. For example, when $E_2$ is providing 0% of the stimulation, the modifying function provides a value of 1. As $E_2$ provides a greater relative percentage of stimulation, the modifying function value increases, until it equals $M_2$ when $E_2$ is providing 50% of the stimulation. As $E_2$ transitions to provide more than 50% of the stimulation, the modifying function value decreases, until it returns to 1 at $E_2=100\%$.

Table 1 below illustrates the value of the modifying function for electrodes $E_1$ and $E_2$ as stimulation is transitioned between them when $M_1=M_2=1.2$

TABLE 1

| % Output of $E_1$ | % Output of $E_2$ | Modifying Function ($E_1$) | Modifying Function ($E_2$) |
|---|---|---|---|
| 100% | 0% | 1.0 | 1.0 |
| 90% | 10% | 1.04 | 1.04 |
| 80% | 20% | 1.08 | 1.08 |
| . | . | . | . |
| . | . | . | . |
| . | . | . | . |
| 50% | 50% | 1.2 | 1.2 |
| . | . | . | . |
| . | . | . | . |
| . | . | . | . |
| 10% | 90% | 1.04 | 1.04 |
| 0% | 100% | 1.0 | 1.0 |

When the modifying function is a linear function, it can also be expressed by the formula:

$$M_N - 2*(M_N-1)*|0.5-X_N|;$$

where N is the electrode number; $M_N$ is the multiplier for electrode $E_N$ and $X_N$ is the percentage output of that electrode $E_N$ from 0 to 1.

In order to maintain a steady level of paresthesia during a transition from $E_1$ to $E_2$, the unmodified output (or output that would be obtained in a simple, linear transition) of each electrode is multiplied by the output of the modifying function for that electrode. The output of $E_1$ is shown in Table 2, where the optimal stimulation level for $E_1$ when that electrode is providing 100% of the stimulation is 2 mA and the multiplier M is 1.2:

TABLE 2

| % Output of $E_1$ | Modifying Function $E_1$ | Unmodified Output of $E_1$ (mA) | Output of $E_1$ After SEQ is Applied (mA) |
|---|---|---|---|
| 100 | 1.0 | 2.0 | 2 |
| 90 | 1.04 | 1.8 | 1.872 |
| 80 | 1.08 | 1.6 | 1.728 |

TABLE 2-continued

| % Output of $E_1$ | Modifying Function $E_1$ | Unmodified Output of $E_1$ (mA) | Output of $E_1$ After SEQ is Applied (mA) |
|---|---|---|---|
| 70 | 1.12 | 1.4 | 1.568 |
| 60 | 1.16 | 1.2 | 1.392 |
| 50 | 1.20 | 1.0 | 1.2 |
| 40 | 1.16 | 0.8 | 0.928 |
| 30 | 1.12 | 0.6 | 0.672 |
| 20 | 1.08 | 0.4 | 0.432 |
| 10 | 1.04 | 0.2 | 0.208 |
| 0 | 1.0 | 0 | 0 |

Table 3 shows the results for $E_2$ where the optimal stimulation level for $E_2$ when that electrode is providing 100% of the stimulation is 2 mA and the multiplier M is 1.2:

TABLE 3

| % Output of $E_2$ | Modifying Function $E_1$ | Unmodified Output of $E_2$ (mA) | Output of $E_2$ After SEQ is Applied (mA) |
|---|---|---|---|
| 0 | 1.0 | 0 | 0 |
| 10 | 1.04 | 0.2 | 0.208 |
| 20 | 1.08 | 0.4 | 0.432 |
| 30 | 1.12 | 0.6 | 0.672 |
| 40 | 1.16 | 0.8 | 0.928 |
| 50 | 1.20 | 1.0 | 1.2 |
| 60 | 1.16 | 1.2 | 1.392 |
| 70 | 1.12 | 1.4 | 1.568 |
| 80 | 1.08 | 1.6 | 1.728 |
| 90 | 1.04 | 1.8 | 1.872 |
| 100 | 1.0 | 2.0 | 2.0 |

Figure 8:
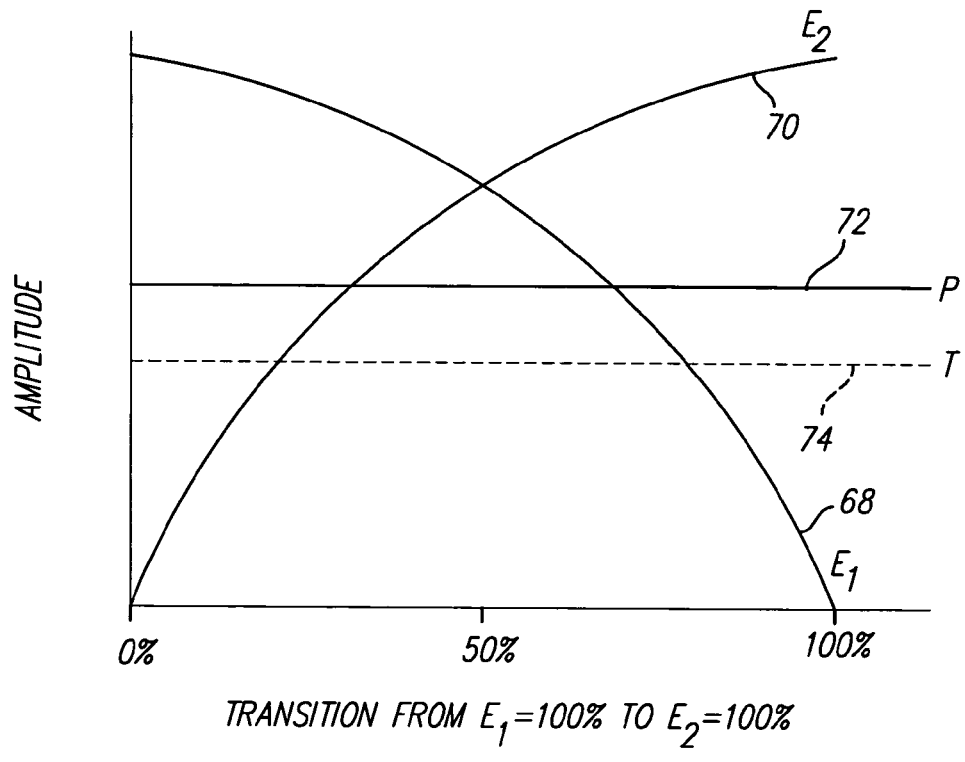
FIG. 8 depicts a graph showing stimulation levels during a transition in stimulation when an SEQ algorithm is used.

FIG. 8 shows the stimulation output of $E_1$ and $E_2$ and the level of stimulation sensed when an SEQ algorithm is used. The output of $E_1$ 68 and the output of $E_2$ 70 are shaped as curves instead of straight lines as in FIG. 5. The stimulation intensity perceived by the patient is shown as a straight line 72. Because of the use of the multiplier to maintain a relatively constant current density during transition, the stimulation perceived is constant, and remains at a level above the threshold stimulation level shown as dashed line T 74.

In practice, line P 72 is not a perfectly straight line due to factors such as the heterogeneity of tissue near the site of stimulation and the approximation of the superposition effect due to the use of a multiplier that is not independently measured for each change in stimulation parameters. However, one of skill in the art will appreciate that the use of an SEQ algorithm that minimizes the number of times that the perceived stimulation drops below the threshold level or rises above the maximum comfortable level during steering will improve the steering process by reducing the need for the patient or clinician to manually adjust the level of stimulation.

Although the example provided above involves a relatively simple transition from one electrode to another, the disclosed method applies equally well when more than two electrodes are involved in a transition. The same modifying functions can be used, and the same functions applying the output of the modifying function to the unmodified output of each electrode can be used. Additionally, the disclosed method applies equally well whether the unmodified transition is made in uniform step sizes (e.g. 5% as shown in Appendix B lines 21 to 41) or non-uniform step sizes (e.g., 2% then 4% then 6%, etc.).

While the invention herein disclosed has been described by means of specific embodiments and applications thereof, numerous modifications and variations could be made thereto by those skilled in the art without departing from the scope of the invention set forth in the claims.

What is claimed is:

1. A method for stimulating tissue using electrodes implanted within a patient, comprising:
   determining a maximum comfortable step size by gradually increasing a step size of test electrical energy transitions applied to the patient until the patient reports that an applied test electrical energy transition is uncomfortable;
   determining a minimum step size;
   selecting a step size that is between the maximum comfortable step size and the minimum step size; and
   incrementally transitioning electrical energy between cathodic ones of the electrodes or incrementally transitioning electrical energy between anodic ones of the electrodes in immediately successive steps, wherein the magnitude of each of the incremental transitions of electrical energy in the immediately successive steps is equal to the selected step size.

2. The method of claim 1, wherein the electrical energy comprises electrical pulses.

3. The method of claim 1, wherein the tissue is spinal cord tissue.

4. The method of claim 1, wherein the electrodes are carried by one or more leads.

5. The method of claim 1, wherein the minimum step size is a desired electrical field shift resolution.

6. The method of claim 1, wherein the minimum step size is a minimum programmable stimulation step size.

7. The method of claim 1, wherein the selecting a step size comprises selecting a plurality of step sizes.

8. The method of claim 1, wherein the step size is a percentage step size.

9. The method of claim 1, wherein the step size is an electrical current amplitude step size.

10. The method of claim 1, wherein the step size is selected by selecting a steering table having the step size.

11. The method of claim 1, wherein the selecting a step size comprises selecting a first step size for the cathodic ones of the electrodes, and selecting a second larger step size for the anodic ones of the electrodes.

12. The method of claim 1, further comprising measuring a perception threshold and a maximum threshold of the patient for the electrodes, wherein selection of the step size is based on the measured thresholds.

13. The method of claim 1, further comprising determining an effective set of stimulation parameters for the electrodes, wherein a first step size is selected for transitioning the electrical energy between the electrodes for a set of stimulation parameters a first number of steps from the effective set of stimulation parameters, and a second larger step size is selected for transitioning the electrical energy between the electrodes for a set of stimulation parameters a second greater number of steps from the effective set of stimulation parameters.

14. The method of claim 1, further comprising determining an ineffective set of stimulation parameters for the electrodes, wherein a first step size is selected for transitioning the electrical energy between the electrodes for a set of stimulation parameters a first number of steps from the ineffective set of stimulation parameters, and a second smaller step size is selected for transitioning the electrical energy between the electrodes for a set of stimulation parameters a second greater number of steps from the ineffective set of stimulation parameters.

15. The method of claim 1, further comprising measuring a perception threshold of the patient for the electrodes, wherein a first step size is selected when transitioning current to or from at least one of the electrodes that produced a first perception threshold measurement, and a second greater step size is selected when transitioning current to or from at least one of the electrodes that produced a second lower perception threshold measurement.

16. The method of claim 1, further comprising creating a current steering table containing a series of values separated by the step size, wherein the electrical energy is incrementally transitioned between the electrodes by stepping through the series of values.

17. The method of claim 1, wherein the electrical energy is incrementally transitioned between the cathodic ones of the electrodes and between the anodic ones of the electrodes using the selected step size.

18. The method of claim 1, further comprising:
   determining a maximum stimulation threshold for an adjustable parameter; and
   determining a perception stimulation threshold for the adjustable parameter.

19. The method of claim 18, wherein the maximum comfortable step size is a maximum change to the adjustable parameter that will not cause discomfort to the patient, and wherein the minimum step size is one of: a smallest change to the adjustable parameter allowable by a stimulation system, and a minimum change to the adjustable parameter that is required to produce a noticeable physiological difference between the effects of two stimulation sets that are separated by the minimum step size.

20. The method of claim 18, wherein the selected step size is at least partially based on the maximum and perception stimulation thresholds.

21. The method of claim 18, wherein the incrementally transitioning comprises incrementally adjusting the adjustable parameter by increments equal to the selected step size.

* * * * *